United States Patent [19]
Barry et al.

[11] Patent Number: 6,126,667
[45] Date of Patent: Oct. 3, 2000

[54] ARTICULATED ABLATION DEVICE

[75] Inventors: Robert L. Barry, Kirkland; Garrett R. Beget, Bellevue, both of Wash.

[73] Assignee: Scimed Life Systems, Inc., Maple Grove, Minn.

[21] Appl. No.: 09/411,135

[22] Filed: Oct. 1, 1999

[51] Int. Cl.⁷ .................................................. A61B 17/00
[52] U.S. Cl. .......................................... 606/159; 606/170
[58] Field of Search .................. 606/1, 108, 159, 606/170, 171, 180; 604/22

[56] References Cited

U.S. PATENT DOCUMENTS

| | | | |
|---|---|---|---|
| 4,445,509 | 5/1984 | Auth .......................................... | 606/159 |
| 5,242,461 | 9/1993 | Kortenbach et al. .................... | 606/159 |
| 5,314,438 | 5/1994 | Shturman ................................. | 606/170 |
| 5,449,369 | 9/1995 | Imran ....................................... | 606/159 |
| 5,925,055 | 7/1999 | Adrian et al. ............................ | 606/159 |
| 5,976,165 | 11/1999 | Ball et al. ................................ | 606/159 |

*Primary Examiner*—Michael Buiz
*Assistant Examiner*—William W. Lewis
*Attorney, Agent, or Firm*—Christensen O'Connor Johnson & Kindness PLLC

[57] ABSTRACT

An ablation device has a burr assembly that is articulated to allow the burr to rotate relative to a longitudinal axis of the driveshaft. The burr is formed in two parts. An inner burr member is coupled to a rotatable driveshaft and has an arcuate region distal to the driveshaft. An outer burr member has an inner cavity in which the inner burr member is positioned. The outer burr member is keyed to the inner burr member, such that the outer burr member rotates with rotation of the driveshaft and inner burr member. However, an inner surface of the outer burr member contacts the arcuate portion of the inner burr member, such that the outer burr member is free to pivot about the arcuate surface of the inner burr member, relative to a longitudinal axis of the driveshaft. Aligned passageways are provided in the driveshaft and inner and outer burr members, to allow a guide wire to extend therethrough. Alternatively, the burr is made of an elastomeric material, and a passageway extends longitudinally through the burr. A bearing positioned in a distal end of the passageway is longitudinally spaced from a collet positioned in a proximal end of the passageway. Given the articulated nature of the burr assembly, the ability of the guide wire to bend, unhindered by the burr assembly, is improved, thereby enhancing the ability of the guide wire and burr assembly to remain centered within a vessel lumen.

13 Claims, 2 Drawing Sheets

ARTICULATED ABLATION DEVICE

FIELD OF THE INVENTION

This invention relates to apparatus for ablating unwanted material from a patient's vasculature.

BACKGROUND OF THE INVENTION

Vascular diseases, such as atherosclerosis and the like, have become quite prevalent in the modern day. These diseases may manifest themselves in a number of ways, often requiring different forms or methods of treatment for curing the adverse effects of the diseases. For example, vascular diseases may take the form of deposits or growths, also known as a stenosis, in a patient's vasculature. These deposits may restrict, in the case of a partial occlusion, or, stop, in the case of a total occlusion, blood flow to a certain portion of the patient's body. This can be particularly serious if, for example, such an occlusion occurs in a portion of the vasculature that supplies vital organs with blood or other necessary fluids.

To treat these diseases, a number of different therapies have been developed. For example, treatment devices have been developed that remove the material occluding a vascular lumen. Such treatment devices, sometimes referred to as atherectomy devices or ablation devices, use a variety of material removal means, such as rotating cutters or ablaters for example, to remove the occluding material. (The term "atherectomy device" as used in the specification refers to ablation devices for use in any portion of a patient's vasculature. Thus, while the atherectomy devices provided in accordance with preferred embodiments of the present invention are well suited for use in the coronary arteries, their use is not limited to the coronary arteries.) The material removal device, such as a rotatable burr, is typically rotated via a driveshaft that extends out of the vasculature of the patient and to an electric motor.

In operation, an ablation device is typically advanced over a guide wire placed in vivo until the material removal device is positioned just proximal to the stenosis. A motor, pneumatically driven rotor, or other similar device is used to rotate the driveshaft and the material removal device, and the material removal device is moved through the stenosis. The material removal device removes the occluding material from the vessel, rather than merely displacing or reforming the material as in a balloon angioplasty procedure.

A potentially negative characteristic for all atherectomy devices is the unwanted ablation of a vessel wall by the device. This can occur when the material removal device improperly engages the vessel wall, for example when the material removal device is not oriented substantially parallel to the axis of the vessel. In this situation, the material removal device (e.g., cutter or abrasive ablater) may engage the vessel wall and cause unwanted ablation thereto.

Similarly, unwanted ablation may also occur if undue pressure is applied to the vessel wall. More particularly, some ablative burrs are designed to differentiate between inelastic and elastic material, removing inelastic material while leaving elastic material untreated. If sufficient pressure is applied to the vessel wall, the pressure may cause the otherwise elastic tissue to become inelastic, making it more susceptible to ablation. However, as discussed above, the ablation device or burr is typically advanced over a guide wire which follows a tortuous path through the patient's vasculature. Conventional ablation devices commonly straighten the guide wire, rather than simply following the guide wire, which results in additional pressure being applied to the vessel wall.

Given the above-discussed considerations, it would be desirable to provide an atherectomy device that reduces the risk of damage to a vessel wall and/or an in vivo stent. In particular, it would be advantageous to provide an atherectomy device that aligns the burr cutting action with a path through the stenosed vessel while removing unwanted material without causing excessive pressure or wear on the vessel walls. The present invention fulfills these needs, and provides further related advantages.

SUMMARY OF THE INVENTION

Briefly, the present invention provides an improved ablation device that reduces the risk of unwanted ablation of a vessel wall. In a preferred embodiment, the ablation device comprises a rotatable burr coupled to a rotatable driveshaft. The burr is configured such that the burr is free to rotate relative to a longitudinal axis of the driveshaft.

In a first preferred embodiment, the burr is formed in two pieces, namely an inner burr member coupled to the driveshaft and an outer burr member coupled to and surrounding the inner burr member. More particularly, the inner burr member has a straight segment coupled to the driveshaft and an arcuate or ball-shaped portion positioned distal to the driveshaft. The outer burr member is formed as a socket or shell having an outer surface provided with means for ablating unwanted material. For example, a portion of the outer surface is provided with abrasive particles, such as diamond grit, as is known in the art. The outer burr member has an inner cavity in which the inner burr member is positioned. The outer burr member is swaged or formed to have an inner surface of the cavity that conforms to and is in contact with segments of the arcuate portion of the inner burr member. As such, the outer burr member is free to pivot about the inner burr member, relative to a longitudinal axis of the driveshaft. To reduce friction between the outer burr member and inner burr member, the arcuate surface of the inner burr member is coated, for example, with Teflon®.

Although the inner burr and outer burr members may be coupled together in a variety of ways, in a preferred embodiment, a post provided on an outer surface of the arcuate portion of the inner burr member is positioned within a recess provided in the inner surface of the cavity of the outer burr member. The interaction of the post and recess keys the outer burr member to the inner burr member, such that rotation of the driveshaft and inner burr member is translated to the outer burr member. However, the fit between the post and recess is sufficiently loose to allow the outer burr member to still move along the outer surface of the inner burr member, relative to the longitudinal axis of the driveshaft. In this manner, the outer burr member and inner burr member have a "ball and socket" configuration that allows a distal tip of the outer burr member to move independently of a proximal end of the outer burr member.

An aperture provided in the distal end region of the outer burr member is aligned with an opening extending through the inner burr member and with a longitudinal passageway extending through the driveshaft. As a result, a guide wire may extend through the driveshaft, inner burr member and outer burr member. As discussed above, the outer burr member is loosely affixed to the driveshaft via the inner burr member, allowing the outer burr member to pivot relative to a longitudinal axis of the driveshaft. The ablation device therefore is better able to turn through a patient's vasculature, and is less likely to straighten the guide wire extending therethrough, as compared to conventional devices. By increasing the likelihood of simply following the guide wire, rather than straightening the guide wire, the guide wire and burr remain more centered within the vessel lumen, thereby reducing pressure placed on the vessel wall. By reducing pressure placed on the vessel wall, the vessel wall remains in an elastic state, making it less likely to be ablated.

It is believed that a significant amount of pressure applied to a vessel wall while rounding highly angulated anatomy is caused by a conventional burr's straightening effect on the guide wire. The ablation device provided in accordance with a preferred embodiment of the present invention reduces the straightening effect, which in turn reduces the pressure applied to the vessel wall, which likewise reduces unwanted ablation. To further enhance the ability of the guide wire to follow the tortuous path of a patient's vasculature, without interference from the burr, the opening provided in the inner burr member flares outward relative to the longitudinal axis of the driveshaft, distal to the driveshaft.

Because the outer burr member is free to pivot relative to a longitudinal axis of the driveshaft, the proximal end of the outer burr member adjacent the driveshaft may shift outward to either side of the driveshaft. The position of the proximal end of the outer burr member relative to the longitudinal axis of the driveshaft may make the retraction of the ablation device more difficult. Therefore, in a preferred embodiment, in order to facilitate removal of the device, a shroud is coupled to the driveshaft surrounding a proximal end region of the outer burr member. An outer surface of the shroud tapers radially outward from the driveshaft to the outer surface of the outer burr member, thereby presenting a smoothly contoured surface to the vessel wall as the device is retracted through the patient's vasculature.

In another preferred embodiment of the present invention, a burr having any selected exterior profile and size is formed of an elastomeric material. An outer surface of the burr is provided with means for ablating unwanted tissue, for example with diamond grit. The body of the burr is provided with a passageway extending therethrough along a longitudinal axis of the burr. A distal end of the passageway is formed to create a first cavity that receives a bearing. A proximal end of the passageway is formed to create a second cavity that receives a collet, the collet surrounding and being coupled to an exterior circumference of a rotatable driveshaft. The collet and bearing are spaced longitudinally by a central region of the passageway, an inner surface of the central region being defined by the elastomeric material of the burr. An opening extends axially through the bearing, aligned with the passageway, thereby allowing a guide wire to extend through the driveshaft, central region of the passageway, and bearing. The flexible, elastomeric burr is molded or press fit over the collet, thereby coupling the burr to the rotatable driveshaft. However, given the elastomeric nature of the burr, and the gap existing between the collet and bearing created by the central region of the passageway, the burr is relatively flexible, thereby allowing the bearing and distal end of the burr to move independently of the collet and proximal end of the burr. Similar to the embodiment described above, the burr is therefore better able to turn through a patient's vasculature, and is less likely to straighten the guide wire extending therethrough. By increasing the likelihood of simply following the guide wire, rather than straightening the guide wire, the guide wire and burr remain more centered within the vessel lumen, thereby reducing the risk of unwanted ablation.

BRIEF DESCRIPTION OF THE DRAWINGS

The foregoing aspects and many of the attendant advantages of this invention will become more readily appreciated as the same becomes better understood by reference to the following detailed description, when taken in conjunction with the accompanying drawings, wherein.

DETAILED DESCRIPTION OF THE INVENTION

An ablation device provided in accordance with preferred embodiments of the present invention is illustrated in FIGS. 1–4. Generally, the ablation device 10 includes a driveshaft 11 and burr assembly 35. As discussed in greater detail below, ablation device 10 is configured to allow a guide wire 13 to pass therethrough, along a longitudinal axis of the device. In operation, guide wire 13 is percutaneously inserted through the vasculature of a patient, and past the targeted occlusion site. Ablation device 10 is slid over guide wire 13 until burr assembly 35 is positioned just proximal to the occlusion site. A guide catheter may be used to assist in the positioning of both guide wire 13 and ablation device 10, as is known in the art. The proximal end of driveshaft 11 remains outside the patient's body and is attached to an electric motor or turbine (not shown). The motor rotates ablation device 10 while it is advanced distally through the occlusion site to ablate occluding material.

Figure 1:
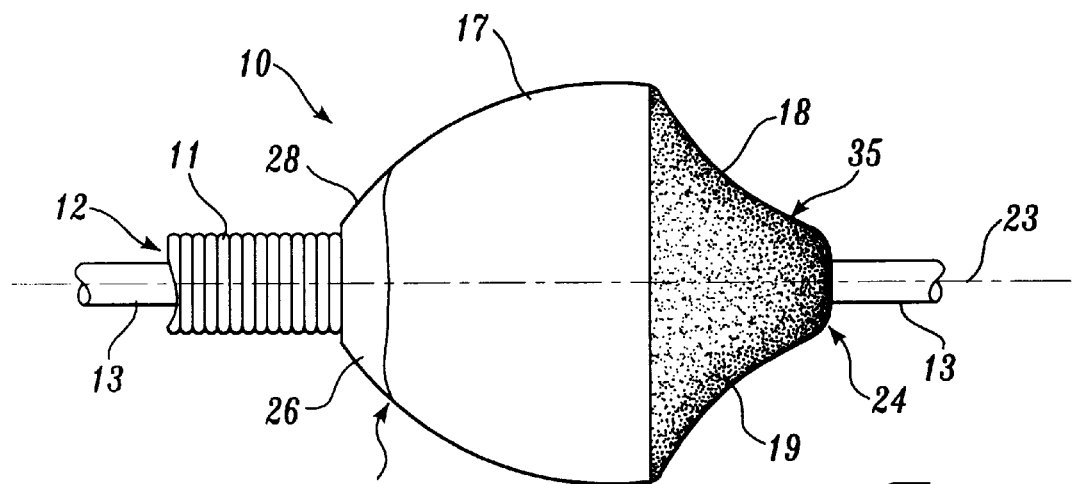
FIG. 1 is a side elevational view of an ablation device provided in accordance with a preferred embodiment of the present invention.
Figure 2:
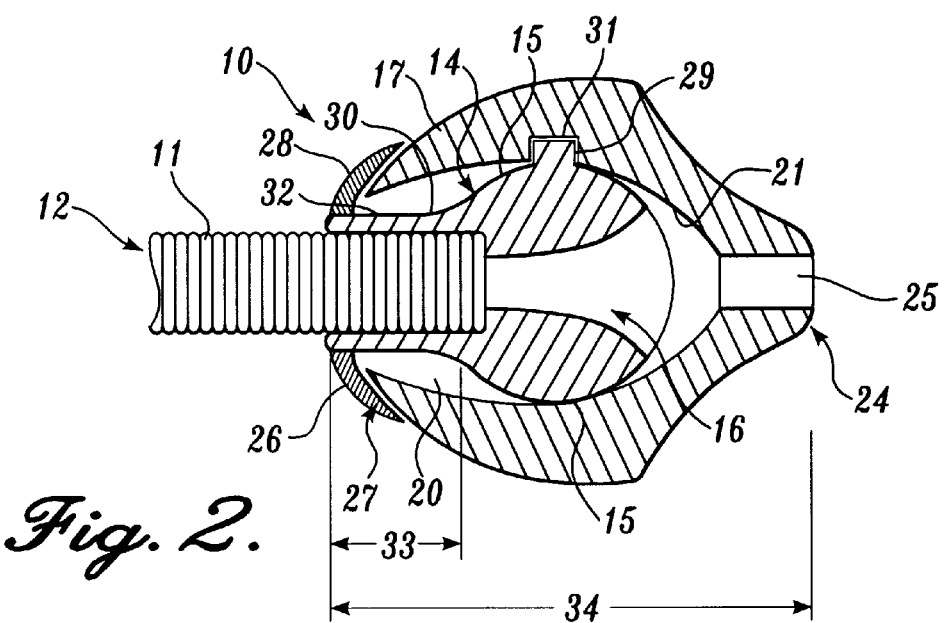
FIG. 2 is a partial cross-sectional elevational view of the device of FIG. 1.
Figure 3:
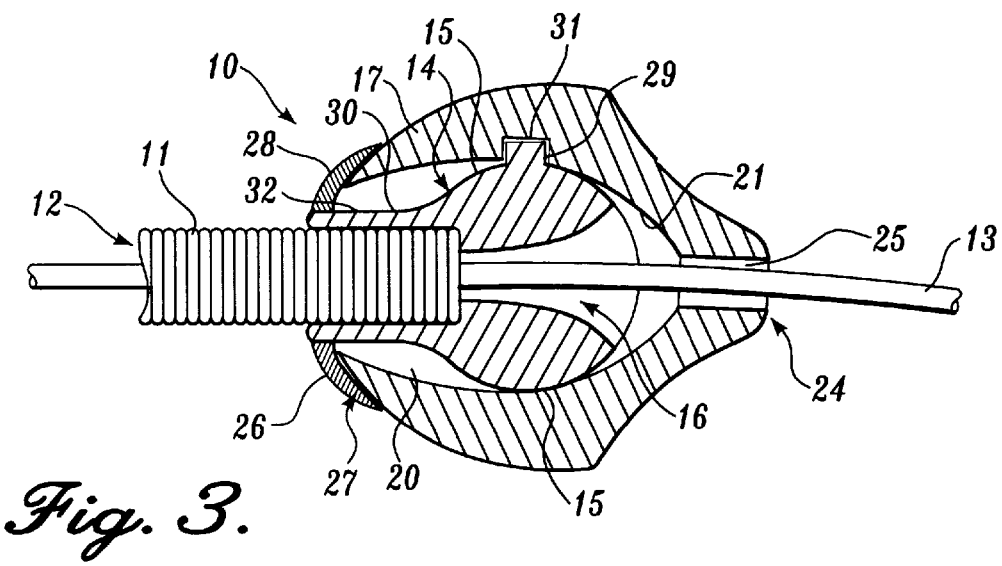
FIG. 3 is a partial cross-sectional elevational view of the device shown in FIG. 1 following the path of a guide wire.

In a first preferred embodiment, as illustrated in FIGS. 1–3, driveshaft 11 has a longitudinal passageway, or lumen 12 through which a guide wire 13 may extend. Burr assembly 35 is comprised of an inner burr member 14 and outer burr member 17. Inner burr member 14 is in the form of a bulb having a sleeve 32 into which a distal portion of driveshaft 11 is inserted. Sleeve 32 forms a relatively short, straight segment that is coupled to driveshaft 11. Although this may be achieved in a variety of ways, in a preferred embodiment, sleeve 32 is laser welded to driveshaft 11. Also, in a preferred embodiment, a length 33 of sleeve 32 is no more than one-third the length 34 of outer burr member 17. The bulb or arcuate portion 15 of inner burr member 14 is generally spherical with an opening or lumen 16 extending therethrough, aligned with longitudinal passageway 12. Lumen 16 has a diameter that increases toward the distal end of the inner burr member such that the lumen is flared open.

As best seen in FIGS. 1 and 2, outer burr member 17 has an outer surface 18 provided with means 19 for ablation. For example, outer surface 18 may be provided with an abrasive, such as diamond grit, as is known in the art. In a preferred embodiment, diamond chips approximately 2–25 microns in size are used. Outer burr member 17 may be provided with other ablation means, for example, cutting blades, or any other ablative means. Outer burr member 17 may also be of any selected shape and size.

In a preferred embodiment, as best seen in FIG. 3, outer burr member 17 has an inner cavity or socket 20, in which inner burr member 14 is positioned. This may be accomplished by either swaging outer burr member 17 onto inner burr member 14 or forming outer burr member 17 in two parts and laser welding the two halves around inner burr member 14. An inner surface 21 of cavity 20 is arcuately contoured to be in contact with the curved outer surface of inner burr member 14. Given the relative size of inner cavity 20 and contact with the arcuate surface of the inner burr member 14, outer burr member 15 is free to pivot about the outer, arcuate surface of inner burr member 14 relative to a longitudinal axis 23 of driveshaft 11.

Although outer burr member 17 is free to move relative to driveshaft 11, it is necessary to couple the outer burr member to driveshaft 11 in order to transfer rotation from driveshaft 11 to outer burr member 17. While this may be accomplished in a variety of ways, in a presently preferred embodiment, a post 29 is provided on an outer surface 30 of arcuate portion 15 of inner burr member 14. A recess 31 is provided in inner surface 21 of inner cavity 20 aligned with post 29. Post 29 is positioned within recess 31 to couple inner burr member 14 and outer burr member 17 together, such that rotation of driveshaft 11 causes both inner burr member 14 and outer burr member 17 to rotate. However, the fit between post 29 and recess 31 is sufficiently loose to still allow outer burr member 17 to rock or pivot about the arcuate surface of inner burr member 14. It will be understood that the fit or relative size of the post 29 and recess 31 dictates the range of motion of outer burr member 17. To reduce friction between inner member 14 and interior surface 21 of outer burr member 17, the inner burr member 14 is *ed with a low friction coating. Although a variety of coatings may be used, in a preferred embodiment, the coating is Teflon®. Also, in a preferred embodiment, inner burr member 14 made from stainless steel and outer burr member 17 is made from brass, although alternatively, inner burr member 17 may be made from brass and outer burr member 17 made from stainless steel.

As further seen in FIGS. 1–3, a shroud 26 is coupled to driveshaft 11 surrounding a proximal end region 27 of outer burr member 17. An outer surface 28 of shroud 26 tapers radially outward from driveshaft 11 to outer surface 18 of outer burr member 17. In this manner, outer surface 28 of shroud 26 presents a smoothly contoured surface to the vessel wall as ablation device 10 is withdrawn from the patient's vasculature. Because outer burr member 17 is free to move relative to driveshaft 11, proximal end region 27 of outer burr member 17 may be displaced to one side or the other of driveshaft 11, relative to a longitudinal axis of the driveshaft. Shroud 26 prevents the displaced proximal end of outer burr member 17 from catching on the artery walls as the device is withdrawn from the patient. Although shroud 26 may be made of a variety of materials, in a preferred embodiment, it is made of medical grade silicone.

As best seen in FIG. 3, distal end region 24 of outer burr member 17 is provided with an aperture 25, aligned with opening 16 in inner burr member 14 and longitudinal passageway 12 of driveshaft 11, thereby allowing guide wire 13 to extend through the entire ablation device 10. In a preferred embodiment, opening 16 of inner burr member 14 flares outward relative to the longitudinal axis of driveshaft 11, distal to driveshaft 11. This configuration further facilitates the guide wire's ability to bend as necessary to remain centered within the vessel lumen as it works its way through the patient's vasculature, without interference and undesirable straightening by the burr assembly 35. By improving the ability of guide wire 13 to bend as necessary, and by minimizing the likelihood of burr assembly 35 straightening guide wire 13, both guide wire 13 and burr assembly 35 are more likely to remain centered in the vessel, thereby reducing contact and undesirable pressure against the vessel wall.

Figure 4:
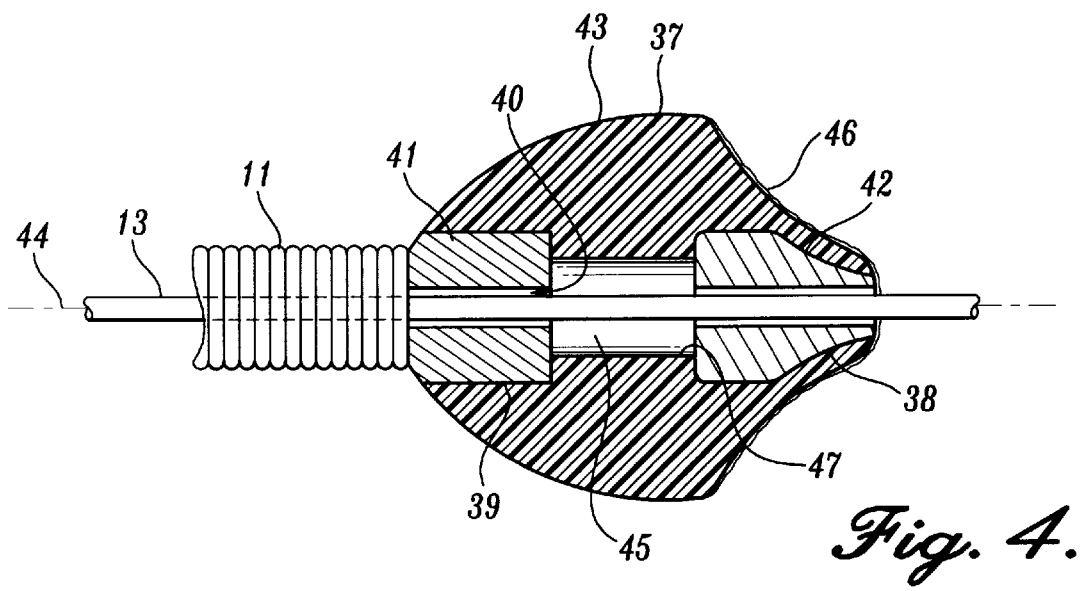
FIG. 4 is a partial cross-sectional elevational view of an ablation device provided in accordance with another preferred embodiment of the present invention.

In an alternative preferred embodiment, as illustrated in FIG. 4, a burr 37 is made of an elastomeric material. Although a variety of materials may be used, in a preferred embodiment, burr 37 is made from urethane, having a hardness of 30–70 Shore A. Burr 37 may have any desired outer contour and size. Similar to the embodiment described above, an outer surface 43 of burr 37 is provided with means for ablating unwanted tissue. Although a variety of ablative devices may be used, in a preferred embodiment, outer surface 43 is provided with diamond grit 46, and preferably, small diamond chips approximately 2–25 microns in size.

In a presently preferred embodiment, abrasive 46 is secured to burr 37 by creating a thin base layer of silver using vacuum deposition techniques. Once the base layer is applied to burr 37, a layer of metal such as nickel having a slurry of diamond particles disposed therein can be plated to the base layer using an electro- or electroless plating method as is done with conventional burrs. In some instances, it may be desirable to etch or mask a portion of burr 37 with a pattern of dots or other shapes so that the base layer does not completely surround burr 37. In addition to electroplating, it is believed that other techniques could be used to secure abrasive 46 to burr 37, such as by using an adhesive or chemically bonding sites on the outer surface of burr 37 to which metal ions such as copper, silver, gold, or nickel may bond. These sites may be bonded to outer surface 43 using a high-vacuum plasma system or by incorporating chemicals (such as carbon, silver, etc.) with the elastomer prior to the formation of burr 37. Alternatively, it is believed that pulse cathode arc ion deposition could be used to incorporate bonding sites on the outer surface 43 of the elastomer.

A passageway 40 extends through burr 37, along a longitudinal axis 44. A distal end of passageway 40 is formed to provide a first cavity 38 that receives a bearing 42. Alternatively, burr 37 may be formed around bearing 42. Although a variety of materials may be used, in a preferred embodiment, bearing 42 is made of brass, to provide a bearing surface for guide wire 13. Use of bearing 42 reduces friction and heat generation, and minimizes the risk of damage to guide wire 13 that may occur if guide wire 13 is allowed to directly contact rotating burr 37. A proximal end of passageway 40 is shaped to provide a second cavity 39 that receives a collet 41. Collet 41 extends around an outer circumference of driveshaft 11 and is coupled thereto. In a preferred embodiment, collet 41 is made of stainless steel, and is heat-welded to driveshaft 11. In a preferred embodiment, burr 37 is insert molded around collet 41. Alternatively, burr 37 is press fit around collet 41.

Collet 41 and bearing 42 are spaced longitudinally by a central region 45 of passageway 40. An inner circumference 47 of central region 45 is formed by the elastomeric material of burr 37. Given the interference fit between the elastomeric material of burr 37 and an outer surface of collet 41, the rotation of driveshaft 11 is transferred to the burr 37. However, given the flexible nature of the elastomeric material, and the gap provided between collet 41 and bearing 42 resulting from central region 45 of passageway 40 extending therebetween, burr 37 is flexible, thereby allowing the bearing 42 and distal end of burr 37 to move independently of collet 41 positioned in the proximal end of burr 37.

An opening extends through bearing 42, aligned with passageway 40, such that guide wire 13 may extend through entire ablation device 10 along a longitudinal axis. The flexibility of burr 37 improves the ability of burr 37 to follow guide wire 13 around the curves and bends of a patient's vasculature, without interfering with guide wire 13. By improving the ability of guide wire 13 to bend as necessary, and by minimizing the likelihood of burr 37 straightening guide wire 13, both guide wire 13 and burr 37 are more likely to remain centered in the vessel, thereby reducing contact and undesirable pressure against the vessel wall.

An improved ablation device has been shown and described. From the foregoing, it will be appreciated that although embodiments of the invention have been described herein for purposes of illustration, various modifications may be made without deviating from the spirit of the invention. Thus, the present invention is not limited to the embodiments described herein, but rather is defined by the claims which follow.

The embodiments of the invention in which an exclusive property or privilege is claimed are defined as follows:

1. An ablation device comprising:
    a driveshaft having a first longitudinal passageway through which a guide wire may extend; and
    a rotatable burr coupled to the driveshaft, the burr being free to pivot relative to a longitudinal axis of the driveshaft, a second passageway extending through the burr and aligned with the first passageway to allow a guide wire to extend therethrough.

2. The ablation device according to claim 1, wherein the burr has an inner burr member that is coupled to the driveshaft and that has a generally spherical outer surface, and an outer burr member having an outer surface provided with means for ablating unwanted material and having an inner cavity in which the inner burr member is positioned, an inner surface of the inner cavity being in contact with the spherical outer surface of the inner burr member such that the outer burr member is free to pivot about the inner burr member relative to a longitudinal axis of the driveshaft.

3. The ablation device according to claim 1, wherein the burr is formed of an elastomeric material and further comprises a bearing positioned in a distal end of the second passageway and a collet positioned in a proximal end of the second passageway, the collet and bearing being spaced by a central region of the second passageway, an inner circumference of the central region being formed by the elastomeric material of the burr, the collet being coupled to the driveshaft.

4. An ablation device comprising:
    a driveshaft having a longitudinal passageway through which a guide wire may extend;
    an inner burr member coupled to the driveshaft and having an arcuate portion positioned distal to the driveshaft and an opening extending through the inner burr member aligned with the longitudinal passageway of the driveshaft; and
    an outer burr member having an outer surface provided with means for ablating unwanted material and having an inner cavity in which the inner burr member is positioned, an inner surface of the inner cavity being in contact with the arcuate portion of the inner burr member such that the outer burr member is free to pivot about the inner burr member relative to a longitudinal axis of the driveshaft, a distal end region of the outer burr member being provided with an aperture aligned with the opening in the inner burr member and the longitudinal passageway of the driveshaft to allow a guide wire to extend therethrough.

5. The device according to claim 4 further comprising:
    a shroud coupled to the driveshaft and surrounding a proximal end region of the outer burr member, the shroud having an outer surface that tapers radially outward from the driveshaft to the outer surface of the outer burr member.

6. The device according to claim 5, wherein the shroud is made from medical grade silicone.

7. The device according to claim 4 further comprising:
    a post provided on an outer surface of the arcuate portion of the inner burr member and a recess provided in the inner surface of the inner cavity aligned with the post, the post being positioned within the recess to couple the inner burr member and the outer burr member together.

8. The device according to claim 4, wherein the opening in the inner burr member flares outward relative to the longitudinal axis of the driveshaft distal to the driveshaft.

9. The device according to claim 4, wherein a segment of the inner burr member is coupled to the driveshaft, a length of the segment being no more than one third of the length of the outer burr member.

10. The device according to claim 9, wherein the segment of the inner burr member is welded to the driveshaft.

11. The device according to claim 4, wherein an outer surface of the arcuate portion of the inner burr member is provided with a coating to reduce friction between the inner burr member and the outer burr member.

12. An ablation device comprising:
    a driveshaft having a longitudinal passageway through which a guide wire may extend;
    an inner burr member coupled to the driveshaft and having a generally spherical outer surface and an opening extending through the inner burr member aligned with the longitudinal passageway of the driveshaft, the opening having a diameter that increases toward the distal end of the inner burr member;
    an outer burr member having an outer surface provided with means for ablating unwanted material and having an inner cavity in which the inner burr member is positioned, an inner surface of the inner cavity being in contact with the generally spherical outer surface of the inner burr member such that the outer burr member is free to pivot about the inner burr member relative to a longitudinal axis of the driveshaft, and a distal end region of the outer burr member is provided with an aperture aligned with the opening in the inner burr member and the longitudinal passageway of the driveshaft to allow a guide wire to extend therethrough; and
    a shroud coupled to the driveshaft and surrounding a proximal end region of the outer burr member, the shroud having an outer surface that tapers radially outward from the driveshaft to the outer surface of the outer burr member.

13. The device according to claim 12, wherein a segment of the inner burr member is coupled to the driveshaft, a length of the segment being no more than one third of the length of the outer burr member.

* * * * *